United States Patent [19]

Numano

[11] Patent Number: 5,007,114
[45] Date of Patent: Apr. 16, 1991

[54] HUMIDITY-RETAINING MASK

[75] Inventor: Yasuhiko Numano, Tokyo, Japan

[73] Assignee: Japan Air Lines Co., Ltd., Tokyo, Japan

[21] Appl. No.: 371,975

[22] Filed: Jun. 27, 1989

[30] Foreign Application Priority Data

Jul. 14, 1988 [JP] Japan .................................. 63-173762
Apr. 15, 1989 [JP] Japan ..................................... 1-94329

[51] Int. Cl.⁵ ............................................ A61M 16/00
[52] U.S. Cl. .................................... 2/206; 128/201.13; 128/204.17
[58] Field of Search ....................... 128/201.13, 204.17, 128/206.12, 206.16; 2/206, 9, 173, 205

[56] References Cited

U.S. PATENT DOCUMENTS

| 2,348,108 | 5/1944 | Bulbulian | 128/201.13 |
| 3,814,094 | 6/1974 | De Angelis et al. | 128/201.13 |
| 3,835,853 | 9/1974 | Turner | 128/201.13 |
| 3,982,981 | 9/1976 | Takao et al. | 156/89 |
| 4,136,691 | 1/1979 | Ebeling et al. | 128/201.13 |
| 4,150,671 | 4/1979 | Tiger | 128/201.13 |
| 4,157,090 | 6/1979 | Phillips | 2/206 X |
| 4,196,728 | 4/1980 | Granite | 128/201.13 |
| 4,325,365 | 4/1982 | Barbuto | 128/201.13 |
| 4,327,717 | 5/1982 | Oetjen et al. | 128/201.13 |
| 4,458,679 | 7/1984 | Ward | 128/201.13 |
| 4,620,537 | 11/1986 | Brown | 128/201.13 |

FOREIGN PATENT DOCUMENTS

| 1364599 | 5/1964 | France | 128/201.13 |
| 63-235192 | 9/1988 | Japan | 128/201.13 |
| 0023279 | of 1894 | United Kingdom | 128/201.13 |

Primary Examiner—Peter Nerbun
Attorney, Agent, or Firm—Wenderoth, Lind & Ponack

[57] ABSTRACT

A humidity-retaining mask includes a foldable mask body made of humidity-absorbing sheet material which is folded into a honeycomb structure when the mask is used. The mask body has a recessed portion on the upper side thereof to receive a user's nostril, and ear traps attached to the mask body.

7 Claims, 3 Drawing Sheets

HUMIDITY-RETAINING MASK

BACKGROUND OF THE INVENTION

1. Field of the Invention

The present invention relates to a humidity-retaining mask and, more particularly, to a humidity-retaining mask which is employed in places where it is difficult to maintain or impart moisture in or to the atmosphere.

2. Description of the Related Art

Masks such as those used to prevent users from catching cold, those used for the prevention of pollinosis and dustproof masks have heretofore been known. These masks are so designed as to be used for their respective predetermined purposes, but none of them are formed of a honeycomb structure.

In aircraft, particularly passenger planes, it is difficult to humidify the cabins due to restrictions on weight, a problem of freezing, etc. and therefore crew members and passengers on board airplanes may suffer from the drying of their nasal cavities and throats. In particular, during a long-distance flight, the interior of a plane becomes dry and the drying of the nasal cavities and throats progresses considerably, so that it becomes difficult for some people to breathe. Under these circumstances, airlines have heretofore racked their brains in devising a countermeasure to prevent the drying of air in the planes.

SUMMARY OF THE INVENTION

An object of the present invention is to solve such problems by an extremely simple means. The present invention is devised to prevent the drying of the passengers' nasal cavities and throats without the need to humidify the air in the cabins of the planes. The present invention is based on the principle that moisture which is discharged through human respiration is retained by means of a mask having a special structure, thereby eliminating the necessity for supply or maintaining moisture to or in the air.

According to the present invention, the mask body is formed using a honeycomb structure made of paper so that moisture discharged by breathing is adsorbed in the cells of the honeycomb structure, thereby retaining humidity.

The mask according to the present invention comprises a foldable mask body made of humidity-absorbing sheet material which is folded out into a honeycomb structure when the mask is used, said mask body having a recessed portion on the upper side thereof to contact with the user's nostril, and ear straps attached to the mask body.

Since the honeycomb structure comprises a large number of honeycomb cells, the walls of these cells effectively adsorb moisture discharged by breathing and the moisture adsorbed on the cell walls is released when the user inhales the outside air, and the released moisture is inhaled together with the air.

More specifically, the humidity-retaining mask according to the present invention comprises: a mask body formed by pattern-drawing a honeycomb structure made of Japanese paper, kraft paper, etc. in the form of a substantially elliptical structure having a recessed portion in the upper part thereof and spreading the substantially elliptical structure through an angle of from 180° to 240° around an axis which is parallel with the major axis of the ellipse and which is near a tangent thereto; a deformable metal sheet attached to a surface thereof in order to maintain the angle of development; a mouth pad attached to said surface in such a manner as to cover the metal, sheet; a nose pad attached to a honeycomb structure surface of the defining the recessed portion; and ear straps attached to the left and right sides, respectively, of the mask body.

For better conformity of the mask to the shape and size of the noses of the users, the mask according to the present invention may be modified to comprise a honeycomb structure which consists of a laminate of a plurality of intermittently bonded hygroscopic sheets having parallel and vertically longitudinally extending bonded portions spaced regularly at predetermined intervals in the widthwise direction thereof so that each bonded portion of said hygroscopic sheets is positioned substantially halfway between two laterally adjacent bonded portions and spaced regularly at predetermined intervals in a direction orthogonal to both the widthwise and longitudinal directions, and which is formed concavely with a suitable curvature at the end surface thereof which contacts the nostrils of a user when said mask is worn by him, and to which concave surface the cells in said honeycomb structure are open; a nose pad provided on the outer surface of the foremost sheet in said honeycomb structure so as to extend higher than said concave surface of said honeycomb structure; a fastening strap attached to the outer surface of the rearmost sheet in said honeycomb structure; and a spring adapted to bias said foremost and rearmost sheets in said honeycomb structure to an expanded practically usable state.

In the humidity-retaining mask of the present invention, moisture which is discharged through human respiration is adsorbed in the cells of the honeycomb structure and therefore a supply of moisture to the atmosphere is unnecessary. More specifically, when air is exhaled, the moisture contained in the exhaled air is adsorbed in the cells the honeycomb structure and, when air is inhaled, the moisture adsorbed in the cells is inhaled together with the air to wet the user's nasal cavity and throat.

The humidity absorbing material for forming the honeycomb structure may be paper such as, for example, Japanese paper manufactured from bast fibers. The invention is not limited to such paper, but can also be implemented by any other material as long as it has the ability to absorb and release moisture. It is preferable that the air respired through such material be maintained at a relative humidity within a range of 30 to 85 RH%, more preferably 40 to 70 RH%, in which displeasure would not be felt. For example, a composite material comprising a sponge-like sheet having paper laminated thereon may be used.

Japanese paper, used in Japan since old times, is particularly preferable as the humidity absorbing material. It is manufactured as a sheet by hand or on a machine using bast fibers as the raw material without using any binder, the bast fibers being non-wood fibers represented by paper mulberry, paper bush and Gampi. Japanese paper manufactured in the manner described immediately above has a suitable function of quickly absorbing moisture from air having a high degree of relative, humidity and releasing moisture into air having a relative humidity of nearly zero.

The humidity-retaining effect lasts as long as the user breathes and, therefore, the drying of his nasal cavity and throat is prevented as long as he wears the mask.

DETAILED DESCRIPTION OF THE PREFERRED EMBODIMENTS

The present invention will be better understood from the following description of preferred embodiments to the accompanying drawings.

EXAMPLE 1

Figure 1:
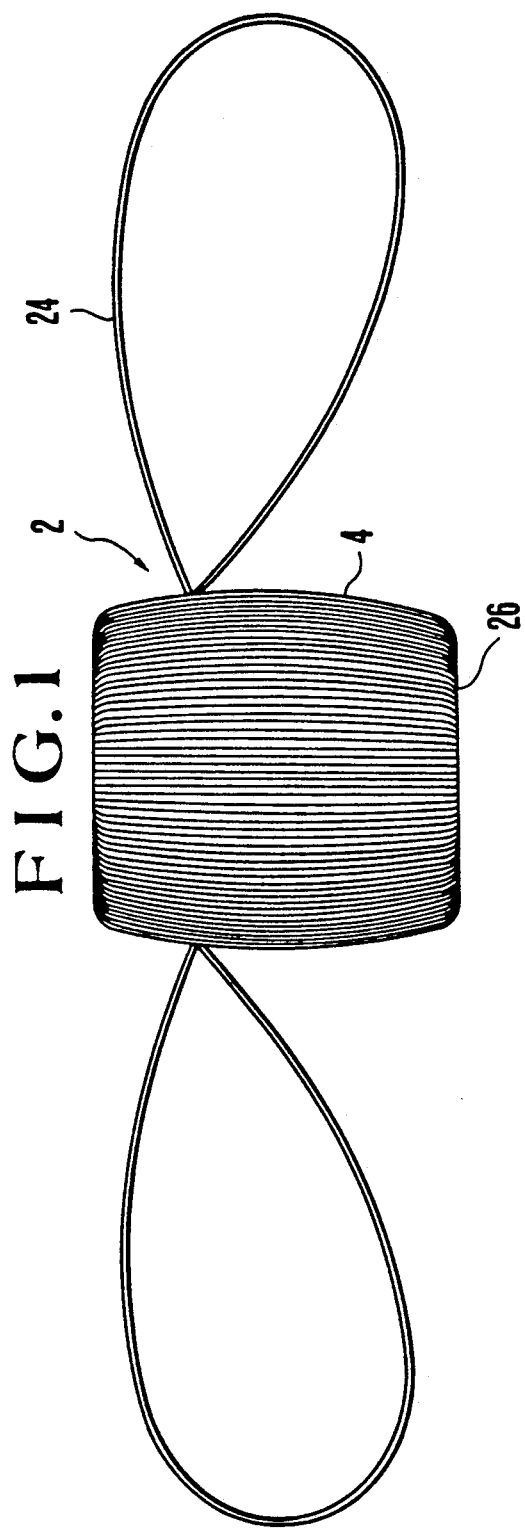
FIG. 1 is a front view of a first embodiment of the humidity-retaining mask according to the present invention.
Figure 2:
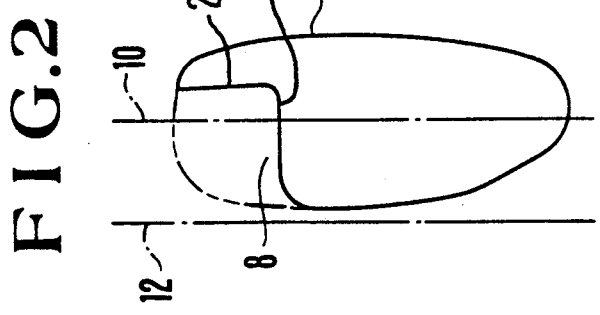
FIG. 2 is a side view of a substantially elliptical structure obtained by punching to form a honeycomb structure that constitutes the body of the mask.

A humidity-retaining mask 2 shown in FIG. 1 has a mask body 4 constituted by a honeycomb structure formed from Japanese paper, kraft paper, etc. More specifically, the mask body is formed in such a manner that a honeycomb structure, which is formed by laminating a large number of blank sheets of Japanese paper, kraft paper, etc. at a predetermined pitch using paste, is pattern-drawn into the form of a subsubstantially elliptical structure 6 having a recessed portion 8 in the upper part thereof, as shown in FIG. 2. The pattern-drawing is effected in such a direction that the cells of the honeycomb structure extend parallel with the major axis 10 of the elliptical structure 6.

Next, with the cut portion 8 disposed at the inner side, the elliptical structure 6 is spread fanwise through an angle of development of from 180° to 240° around an axis 12 which is parallel to the major axis 10 of the ellipse and which is near a tangent thereto, thereby forming a mask body 4. In order to prevent the honeycomb structure from self-closing and maintain the angle of development, a deformable metal sheet 16 such as an aluminum sheet, copper sheet, etc. is secured to the development surface 14 by means of an adhesive.

Figure 5:
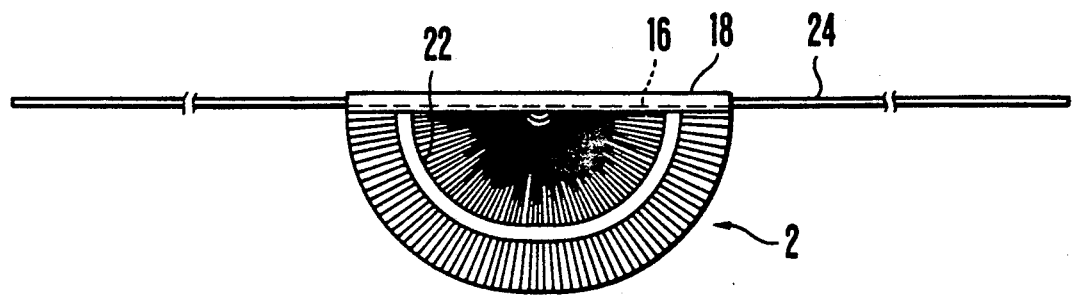
FIG. 5 is a plan view of the humidity-retaining mask.
Figure 6:
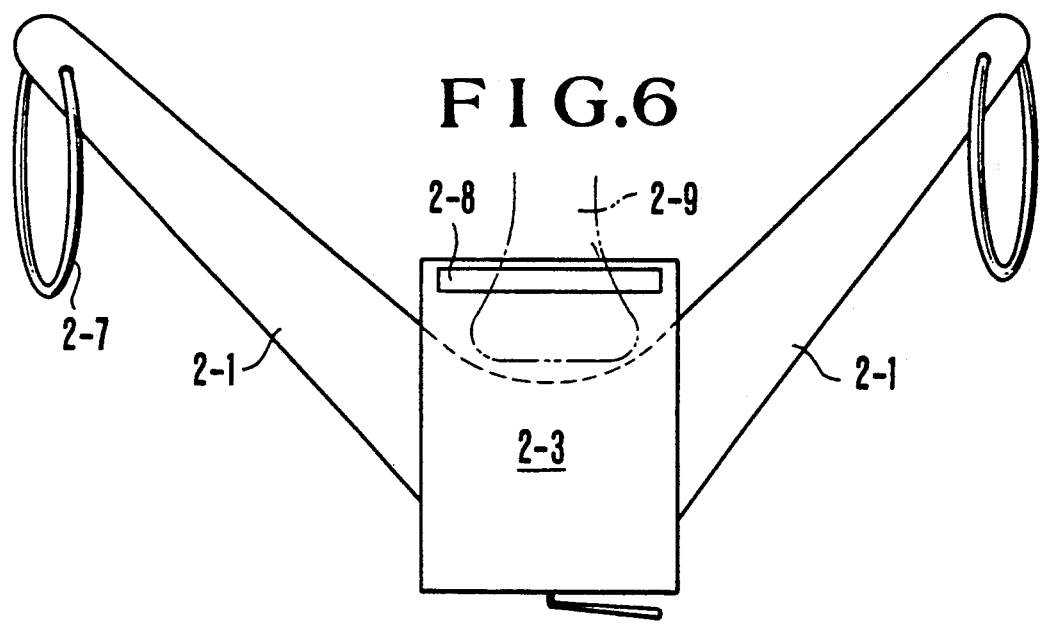
FIG. 6 is a front elevation view of a second embodiment of a humidity-retaining mask, having a honeycomb-forming laminate expanded to form a practically usable opened-cell-carrying structure, according to the present invention.

Further, a mouth pad 18 made of a sponge material is secured to the development surface 14 by means of an adhesive such that the pad 18 covers the metal sheet 16, as shown in FIG. 5.

Figure 3:
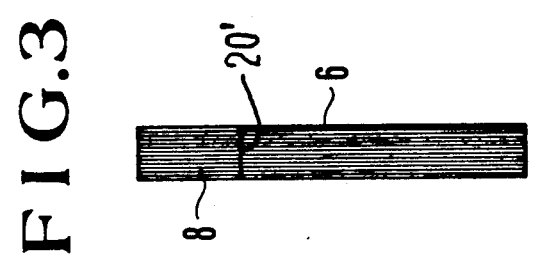
FIG. 3 is a rear view of the substantially elliptical structure shown in FIG. 2.
Figure 4:
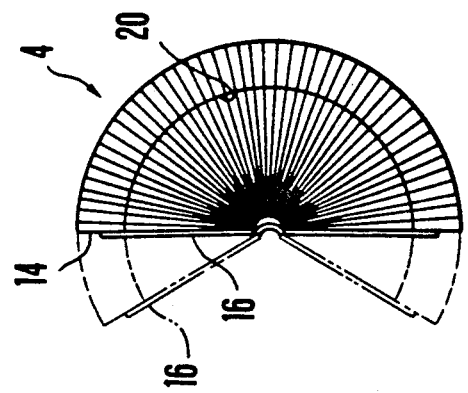
FIG. 4 is a plan view of the substantially elliptical structure shown in FIG. 2 which is in a developed state.

A nose pad 22 made of a sponge material is similarly secured by means of an adhesive to the substantially semicircular development surface 20 of the recessed portion 8 of the substantially elliptical structure 6. Whereas the development surface 20 extends downwardly from an upper surface of the mask body (FIG. 2) so as to be a first surface defining the recessed portion, a second surface 20' defining the recessed portion extends from the development surface 14 at one side of the mask body toward the other side thereof (FIGS. 2, 3).

Finally, ear straps 24 which are resilient rubber strings are attached to the left and right sides, respectively, of the mask body. The ear straps are preferably attached by means of an adhesive at the same time as the mouth pad 18 is secured.

When using the humidity-retaining mask 2, the user is only required to put his nose on the substantially semicircular development surface 20 of the mask body 4 and engage the ear straps 22 with his ears, respectively.

When the user wears the humidity-retaining mask 2, his nostrils face the ends of the cells of the honeycomb structure that constitutes the mask body and the nose pad 22 secured to the substantially semicircular development surface 20 of the body 4 surrounds the tip of the nose. Accordingly, there is no possibility of air from the nostrils leaking from the mask body before passing through the cells thereof when the user breathes.

Thus, air exhaled from the nostrils is discharged from the lower side 26 of the body through the cells of the honeycomb structure, while the outside air is breathed into the nostrils from the lower side of the body through the cells of the honeycomb structure. At this time, moisture contained in the air exhaled from the nostrils is adsorbed in the cells of the honeycomb structure. Accordingly, when the outside air is inhaled, the moisture adsorbed in the cells is released and breathed into the nostrils together with the air inhaled and this moisture wets the user's nasal cavity and throat.

The humidity-retaining mask having the above structural features enables the user to breath considerably easily without the need to supply moisture even in an environment or atmosphere having air which is difficult to moisten.

Further, the humidity-retaining mask is disposable since it has a simple structure and a low production cost.

In addition, the humidity retaining effect lasts as long as the user breathes and, therefore, drying of his nasal cavity and throat is prevented as long as he wears the mask. Thus, the mask has highly advantageous effects in practical use.

EXAMPLE 2

Figure 7:
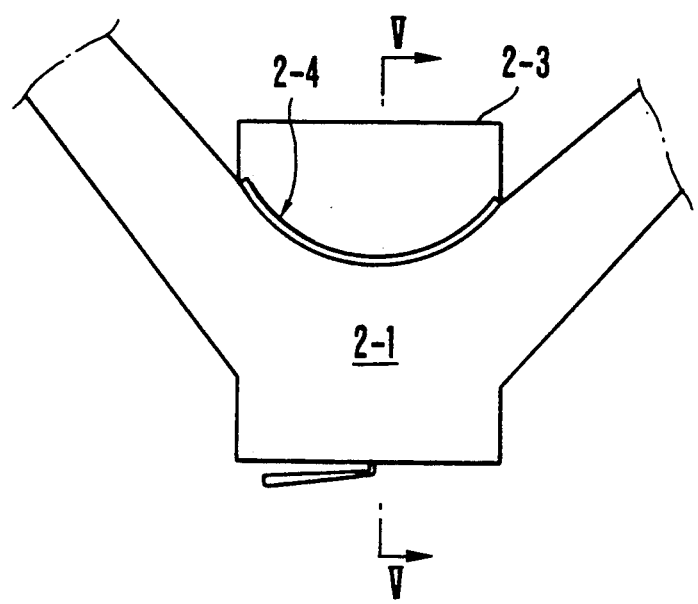
FIG. 7 is a rear elevation view of a principal portion of the humidity-retaining mask.
Figure 8:
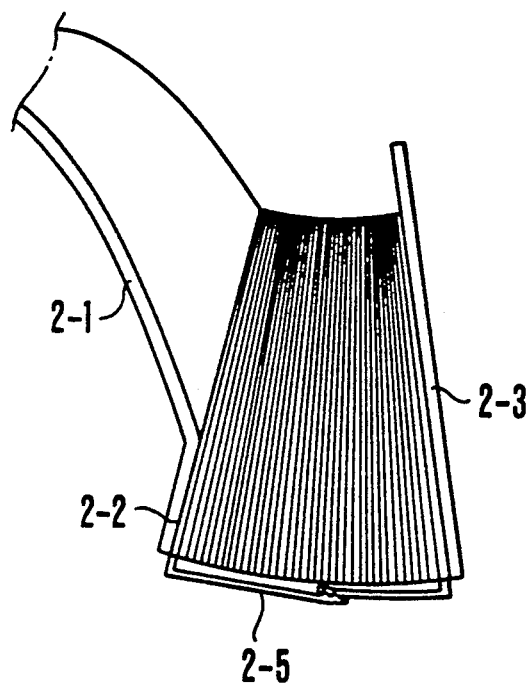
FIG. 8 is an enlarged side elevation view of a principal portion of the humidity-retaining mask.
Figure 10:
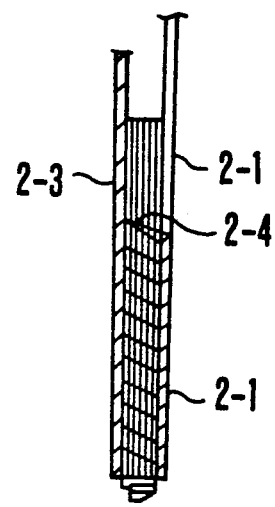
FIG. 10 is a sectional view taken along the line V-V in FIG. 7 and showing the honeycomb-forming laminate not yet expanded to form an opened-cell-carrying structure.
Figure 9:
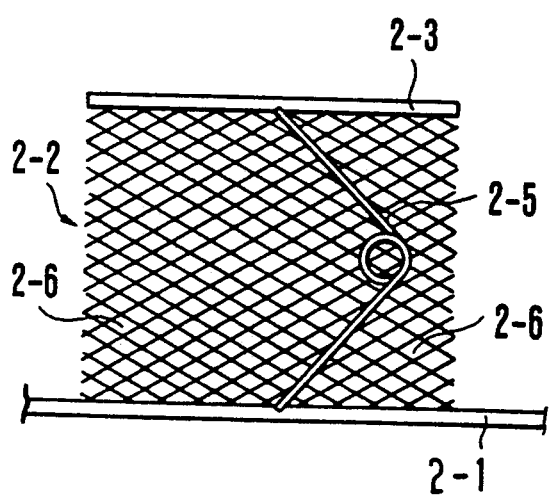
FIG. 9 is an enlarged bottom view of a principal portion of the humidity-retaining mask.

A second embodiment of the present invention will be described by referring to FIGS. 6-11. Reference numeral 2-1 denotes a fastening strap bonded at its central portion to one outer side surface of a honeycomb structure 2-2 (refer to FIGS. 8 and 9) consisting of a laminate of a plurality of pieces of bonded Japanese paper. Reference numeral 2-3 denotes a nose pad bonded to the other side surface of the honeycomb structure 2-2 and extending higher than a concave surface 2-4, in which the upper end openings of the cells in the honeycomb structure are opposed to the nostrils of a user, of the honeycomb structure 2-2. The honeycomb structure 2-2 is biased to an expanded state, i.e., to a cell-opened state as shown in FIGS. 8 and 9, by a formed wire 2-5 attached to the honeycomb structure 2-2 by fixing both of the leg-end portions of the formed wire 2-5 to both of the outer side surfaces of the honeycomb structure 2-2. The cells in the honeycomb structure extend vertically in FIGS. 6-8. If the concave surface 2-4 is inclined downward from the nose pad 2-3 toward the fastening strap 2-1 as shown in FIGS. 7 and 10, it can attain further improved opposed relation with respect to the nostrils of a user when the humidity-retaining mask is worn. Reference numeral 2-7 denotes string loops secured to the free end portions of the fastening strap 2-1 so as to be passed around the ears of a user, 2-8 a shapable plate consisting of a deformable metal sheet and bonded to the upper portion of the outer surface of the nose pad 2-3, and 2-9 the nose of a user.

Figure 11:
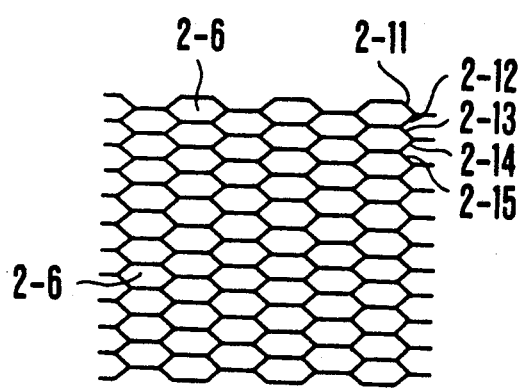
FIG. 11 is a schematic of the honeycomb structure.

FIG. 11 illustrates the honeycomb structure. Referring to the drawing, reference numerals 2-11, 2-12, 2-13, 2-14, 2-15 denote Japanese paper arranged in vertically extending layers and bonded together intermittently.

When the humidity-retaining mask is worn over the nose and mouth of a user with the concave surface 2-4 of the honeycomb structure and the string loops 2-7 on the fastening strap opposed to the nostrils and passed around the ears, respectively, the nose is covered with the nose pad 2-3. The shapable plate 2-8 is then deformed by the fingers so that the nose pad 2-3 consisting of sponge a sponge material comprising an unwoven cloth and a synthetic resin fits the outer surface of the nose as closely as possible. The air exhaled by the user who wears this humidity-retaining mask flows into a plurality of cells open at in the concave surface 2-4 of the honeycomb structure, and is discharged from the lower end openings thereof to the atmospheric air. The air inhaled by the user flows into the interior of the cells from the openings in the lower end surface of the honeycomb structure, and the air discharged from the user end openings thereof enters the nostrils.

With the above structural features, the humidity-retaining mask is capable of being fitted excellently on various types of noses, i.e. noses of different shapes and sizes. Further, the mask is capable of substantially preventing the air exhaled and inhaled by a user from passing through a space other than the spaces defined by the cells in the honeycomb structure, i.e., through a space between the honeycomb structure and the nose of the user, so as to be capable of effectively achieving the humidity-retaining object.

What is claimed is:

1. A humidity retaining mask for humidifying dry air of an environment to be respired by a wearer of the mask, said mask comprising:
    an expandable mask body consisting of a honeycomb structure of moisture absorbing material defining a plurality of tubular cavities when the mask body is in an expanded state, said mask body having a recessed portion in an upper part thereof for accommodating the nostrils of a wearer of the mask and a lower part opposed to said upper part, and said tubular cavities extending between and open at the upper and lower parts of the mask body; and
    ear straps attached to said mask and adapted to extend over the ears of a wearer of the mask to secure said mask body in a position in which the nose of the wearer confronts said recessed portion.

2. A mask as claimed in claim 1, wherein said recessed portion is defined by an upper surface of the mask body that is concave.

3. A mask as claimed in claim 2, and further comprising a nose pad of sponge-like material secured to a front end of said mask body and extending upwardly beyond the upper surface of said mask body so as to abut the tip end of a nose of a wearer of the mask when the nostrils thereof confront said upper surface, and a piece of shapable metal attached to and extending across said nose pad, said piece of shapable metal being deformable by the wearer to conform the nose pad to the shape of the outer surface of the tip of the nose of the wearer.

4. A mask as claimed in claim 1, wherein said mask body has a generally elliptical cross section as taken between said upper and said lower parts thereof,
    said mask body has a development surface at one side thereof that is foldable and is openable, about an axis parallel to the major axis of the elliptical cross section and near a tangent to said development surface, from a folded state to an unfolded state at which an angle of between 180° and 240° is defined by said surface to place said mask body in an expanded state, and
    said recessed portion is defined by a first surface of said mask body extending downwardly form an upper surface of the mask body and a second surface of the mask body extending from the development surface of said mask body toward the other side thereof.

5. A mask as claimed in claim 4, and further comprising a deformable metal sheet attached to said development surface in order to maintain the mask body in said expanded state, a mouth pad attached to said mask body and covering said metal sheet, and a nose pad attached to said mask body and covering said first surface thereof defining said recessed portion.

6. A humidity retaining mask for humidifying dry air of an environment to be respired by a wearer of the mask, said mask comprising:
    a mask body comprising a honeycomb structure consisting of a laminate of a plurality of hygroscopic sheets defining a plurality of openings extending longitudinally therethrough,
    said laminate having a plurality of parallel bonded portions extending in a longitudinal direction and at which bonded portions adjacent said sheets are bonded to one another, said bonded portions being regularly spaced at predetermined intervals in the widthwise direction of the honeycomb structure so that each of said bonded portions is located substantially halfway between two laterally adjacent said bonded portions, and said bonded portions being regularly spaced at predetermined intervals in a direction orthogonal to said widthwise and longitudinal directions,
    said mask body having a concave surface at an upper end thereof for receiving the nostrils of a wearer of said mask, said openings extending longitudinally through said laminate being open at said concave surface;
    a nose pad secured to said mask body over a foremost one of said sheets of said laminate, said nose pad extending upwardly beyond said concave surface so as to abut the tip end of a nose of a wearer of the mask; and
    a fastening strap attached to said mask body so as to secure said mask body to a wearer in a position in which the nostrils of the wearer confront said concave surface.

7. A mask as claimed in claim 6, wherein said fastening strap is secured over a rearmost one of said sheets of said laminate, and further comprising a spring biasing said foremost and said rearmost sheets apart to maintain said honeycomb structure in an expanded state.

* * * * *